United States Patent [19]

Sekine

[11] Patent Number: 4,933,756
[45] Date of Patent: Jun. 12, 1990

[54] EYE FUNDUS CAMERA
[75] Inventor: Akihiko Sekine, Tokyo, Japan
[73] Assignee: Kabushiki Kaisha Topcon, Tokyo, Japan
[21] Appl. No.: 335,322
[22] Filed: Apr. 10, 1989
[30] Foreign Application Priority Data Apr. 12, 1988 [JP] Japan .................................. 63-89607
Apr. 12, 1988 [JP] Japan .................................. 63-89608

[51] Int. Cl.$^5$ ............................................. H04N 7/18
[52] U.S. Cl. ..................................... 358/93; 351/206; 354/62
[58] Field of Search .......... 358/93; 351/206, 208–210; 354/62

[56] References Cited

U.S. PATENT DOCUMENTS

| 4,526,450 | 7/1985 | Suzuki | 351/206 |
| 4,572,627 | 2/1986 | Madate | 351/206 |
| 4,675,736 | 6/1987 | Lehmer | 358/93 |
| 4,717,952 | 1/1988 | Kohayakawa | 358/113 |

Primary Examiner—Howard W. Britton
Attorney, Agent, or Firm—Finnegan, Henderson, Farabow, Garrett & Dunner

[57] ABSTRACT

An eye fundus camera of this invention has a light source for illuminating the fundus of an eye to be tested, an illuminating optical system for projecting illuminating beam from the light source to the eye fundus, and a light receiving optical system for taking out reflected light from the eye fundus through a common optical path with the illuminating optical system. The common optical path has a tilt optical path from a light reflector to the eye, and the tilt optical system can be tilted about the optical center of the light reflector. With the foregoing constitution, the optical axis of the eye fundus camera can be tilted with respect to the optical axis of the eye rapidly and easily. Also, this tilting prevents the tilting of the rotational axis of a polygon mirror, thus enabling to prevent an occurrence of inconvenience due to the tilting of the rotational axis.

16 Claims, 6 Drawing Sheets

EYE FUNDUS CAMERA

BACKGROUND OF THE INVENTION

1. Field of the Invention:

This invention relates to an eye fundus camera used for observing and/or photographing an eye fundus to be tested or subject's retina by projecting illuminating beam thereto.

2. Description of the Prior Art:

As an eye fundus camera of this type, there is one of a laser beam scanning type for example. As this laser beam scanning type eye fundus camera, there can be considered one which includes an illuminating optical system for scanning laser beam, which is emitted by a laser beam source, to a scanning member such as a galvano mirror, etc. and projecting the scanned beam to the subject's retina, and a light receiving optical system for taking out the light reflected by the eye fundus through a common optical path with the illuminating optical system.

In case the eye fundus of a patient is going to be observed or photographed using such the eye fundus camera as mentioned, the central portion of the eye fundus is usually observed and/or photographed in many cases. However, there are some cases where the peripheral portion of the eye fundus is desired to be observed and/or photographed.

As a method for observing and/or photographing the peripheral portion of the eye fundus, several methods are considered such as, for example, a method for spreading an angle of view by attaching a contact lens to the subject's eye, a method for spreading the range of observation and/or photographing by changing the reference scanning position of a galvano mirror and without changing the angle of view of an optical system, etc.

However, in the method using a contact lens, it is required to drop an anesthetic lotion in the subject's eye in order to dilate the pupil thereof. This renders a heavy burden onto a patient. In addition, there is a fear of getting infection.

Also, in the method for changing the reference scanning position of a galvano mirror, although the range of observation and photographing can be spread to some extent, it is impossible to observe and/or photograph the peripheral portion of the eye fundus due to limitation of an objective lens in size.

Therefore, heretofore, the whole eye fundus camera was tilted upwardly or downwardly to tilt the optical axis of the eye fundus camera with respect to the optical axis of the eye when the peripheral portion of the eye fundus was going to be observed and/or photographed.

However, since the eye fundus camera is heavy, it is not easy to tilt the camera.

Also, as an eye fundus camera of a laser beam scanning type, there is one in which a polygon mirror is rotated at a high speed to scan illuminating beam in the horizontal direction and a galvano mirror scans the horizontally scanned scanning beam in the vertical direction.

Since the polygon mirror of this type of eye fundus camera is rotated at a high speed, it produces a gyroscopic moment. As a result, when the eye fundus camera is about to be tilted vertically, the camera is tended to return to its original posture position due to the function of the gyro moment, thus making it difficult to tilt the camera in the desired direction rapidly and easily.

Moreover, in case an air bearing is used as a bearing for this polygon mirror, there is a risk that the rotary shaft of the polygon mirror and the bearing are contacted with each other, thus resulting in breakage thereof. Also, when the whole eye fundus camera is to be tilted in the vertical direction as described, the rotary shaft of the polygon mirror is tilted and load incurred to the bearing of the polygon mirror is one-sided. This results in a cause of one-sided wear of the bearing and thus not desirable.

SUMMARY OF THE INVENTION

The object of the invention is to provide an eye fundus camera, in which the optical axis thereof can be tilted with respect to the optical axis of a subject's eye rapidly and easily, and yet the tilting of the rotational axis of a polygon mirror can be prevented due to the tilting of the optical axis of the eye fundus camera, thus enabling to prevent an occurrence of inconveniences caused by the tilting of the rotational axis.

In order to achieve the above object, an eye fundus camera according to one aspect of the present invention comprises a light source for illuminating an eye fundus to be tested, an illuminating optical system for projecting the light from the light source to the eye fundus, and a light receiving optical system for taking out the light reflected by the eye fundus through a common optical path with the illuminating optical system, the common optical path including a tilt optical path from a light reflector to the objective lens, the tilt optical system being tiltable about the optical center of the light reflector.

Also, an eye fundus camera according to another aspect of the invention comprises a polygon mirror being able to rotate at a high speed in order to scan beam coming from a light source in the horizontal direction, an illuminating optical system for projecting the scanned beam to an eye fundus to be tested, and a light receiving optical system for taking out the light reflected by the eye fundus through a common optical path with the illuminating optical system, a tilt optical path at least from a light reflector within the common optical path to the objective lens being tiltable about the optical center of the light reflector.

Furthermore, an eye fundus camera according to a further aspect of the present invention comprises an illuminating optical system for projecting illuminating beam to an eye fundus from a facing optical member opposite the eye, and a light receiving optical system including the facing optical member and adapted to take out light reflected by the eye fundus through a common optical path with the illuminating optical system, a tilt optical system from the facing optical member of the common optical path to a light reflector within the common optical path being tiltable about the optical center of the light reflector, the light reflector being connected to the tilt optical system as such that the light reflector is tilted in the tilting direction of the tilt optical system through ½ of a tilt angle of the tilt optical system about the optical center of the light reflector.

An eye fundus camera according to a still further aspect of the present invention comprises a polygon mirror being able to rotate at a high speed in order to scan illuminating beam from a light source in the horizontal direction, an illuminating optical system for projecting the scanned beam to the eye fundus from a facing optical member opposite the eye, and light receiving optical system including the facing optical member and adapted to take out reflected light from the eye fundus through a common path with the illuminating optical system, a tilt optical system from the facing optical member of the common optical path to a light reflector within the common optical path being tiltable about the optical center of the light reflector, the light reflector being connected to the tilt optical system as such that the light reflector being tilted in the tilting direction of the tilt optical system through ½ of a tilt angle of the tilt optical system about the optical center of the light reflector.

And, it may be designed as such that the optical members from the polygon mirror to an optical member located immediately before the light reflector can be rotated about the center of rotation of the polygon mirror in the horizontal direction. Also, it may be designed as such that the optical members from the polygon mirror to the light reflector can be rotated about the center of rotation of the polygon mirror.

Furthermore, the light reflector may be a galvano mirror as a scanning member. Also, the light reflector may be a reflecting mirror located immediately after an objective lens.

Also, there may be provided a body which can be moved in the three dimensional direction by a three dimensional moving mechanism, the body being provided with the illuminating optical system and the light receiving optical system and also with interlocking means which, when the tilt optical system is tilted through angle $\theta$ and the position of the tilt optical system is displaced by X,Y in the vertical direction with respect to the eye, automatically causes the body to be moved through displacing quantities X,Y in the vertical and diagonal direction. Furthermore, it may be designed as such that the three dimensional drive mechanism can be driven by a first pulse motor, the tilt optical system can be tilted by a second pulse motor and both the pulse motors can be driven by a CPU as interlocking means.

These and other objects, features and advantages of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of the claims appended hereto.

DESCRIPTION OF THE PREFERRED EMBODIMENT

The embodiment of the present invention will be described hereunder with reference to the accompanying drawings.

FIG. 1 through FIG. 8 are illustrations showing a first embodiment of the present invention.

Figure 1:
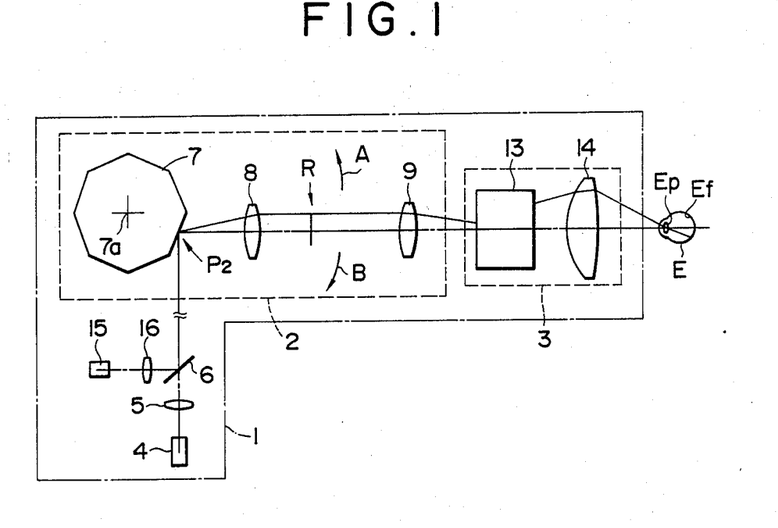
FIG. 1 is a schematic view showing an optical system of an eye fundus camera according to the present invention.

In FIG. 1, 1 denotes a body of an eye fundus camera which can be moved back and forth, rightward and leftward, and upward and downward by a three-dimensional drive mechanism known per se, 2 denotes a first optical part holding member horizontally and pivotally mounted in the body 1 as will be described, 3 denotes a second optical part holding member such as a lens barrel, etc. which is mounted on the first optical part holding member 2 as such that the member 3 can be pivoted in a vertical plane as will be described, and 4 denotes a laser beam oscillator (laser beam source) such as an LD, etc.

The optical system of FIG. 1 includes an illuminating optical system for scanning laser beam emitted by the laser beam oscillator 4 and projecting the scanned beam of light to the eye fundus or subject's retina $E_f$ of an eye to be tested or subject's eye E, and a light receiving optical system for taking out reflecting beam of light reflected by the eye fundus $E_f$ through a common optical path with the illuminating optical path.

The illuminating optical system includes, as optical members, a lens 5, a semitransparent mirror 6, a polygon mirror 7 (first scanning member) acting as a light reflector, variable power lenses 8,9, a galvano mirror 10 (second scanning member) acting as a light reflector, a relay lens 11, a focus lens 12, a reflecting mirror 13 acting as a light reflector, an objective lens 14, etc. (see FIG. 1 through FIG. 3). Moreover, the polygon mirror 7 (first scanning member) and the variable power lenses 8,9 are mounted on the first optical part holding member 2, and the second optical part holding member 2 is mounted on the body 1 as such that the member 2 can be horizontally pivoted about the center of rotation 7a of the polygon mirror 7 as shown by arrows A,B.

And, laser beam emitted by the laser light source 1 is made incident to the polygon mirror 7 through the lens 5 and the semitransparent mirror 6 and is then reflected toward the variable power lens 8 side. At this time, the reflected beam is horizontally scanned by high-speed rotation of the polygon mirror 7. The horizontally scanned beam is reflected by the galvano mirror 10 toward the relay lens 11 side through the variable power lenses 8,9, and then projected to the eye fundus $E_f$ of the eye E for illumination through the relay lens 11, the focus lens 12, the reflecting mirror 13 and the objective lens 14. At this time, the galvano mirror 10 is pivoted through a predetermined angle at a time per each horizontal scanning operation as such that the horizontal scanning beam is moved in the vertical direction to form a scanning plane of the laser beam on the eye fundus $E_f$. 15 denotes a light receiving element. Also, in the figures, $P_o, R_0$ in the position of the eye E denote the positions of the pupil $E_p$ and the eye fundus $E_f$, respectively, $P_1, P_2$ denote positions conjugated with the pupil $E_p(P_o)$ of the eye E, and R denotes a position conjugated with the eye fundus $E_f(R_o)$ of the eye E.

Also, the light receiving system includes a common optical path with the illuminating optical system from the objective lens 14 to the semitransparent mirror 6, and further includes, as an optical part, a lens 18 adapted to guide reflecting beam of light reflected by the semi-transparent mirror 6 to the light receiving element 15.

Moreover, the first optical part holding member 2 is provided with a second optical part holding member 3 such as a lens barrel, etc. mounted thereon as such that the member 3 can be pivoted about the optical center 10a of the galvano mirror 10 along a vertical plane as shown by arrows C,D. And, within the second optical part holding member 3, there are held members for forming the tilt optical system from the galvano mirror 10 to the objective lens 14 of the common optical path, i.e., the galvano mirror 10, the relay lens 11, the focus lens 12, the reflecting mirror, the objective lens 14, etc. Due to the foregoing arrangement, the tilt optical system from the galvano mirror 10 to the objective lens 14 of the common optical path can be pivoted about the optical center 10a of the galvano mirror 10 along the vertical plane as shown by the arrows C,D.

Figure 4:
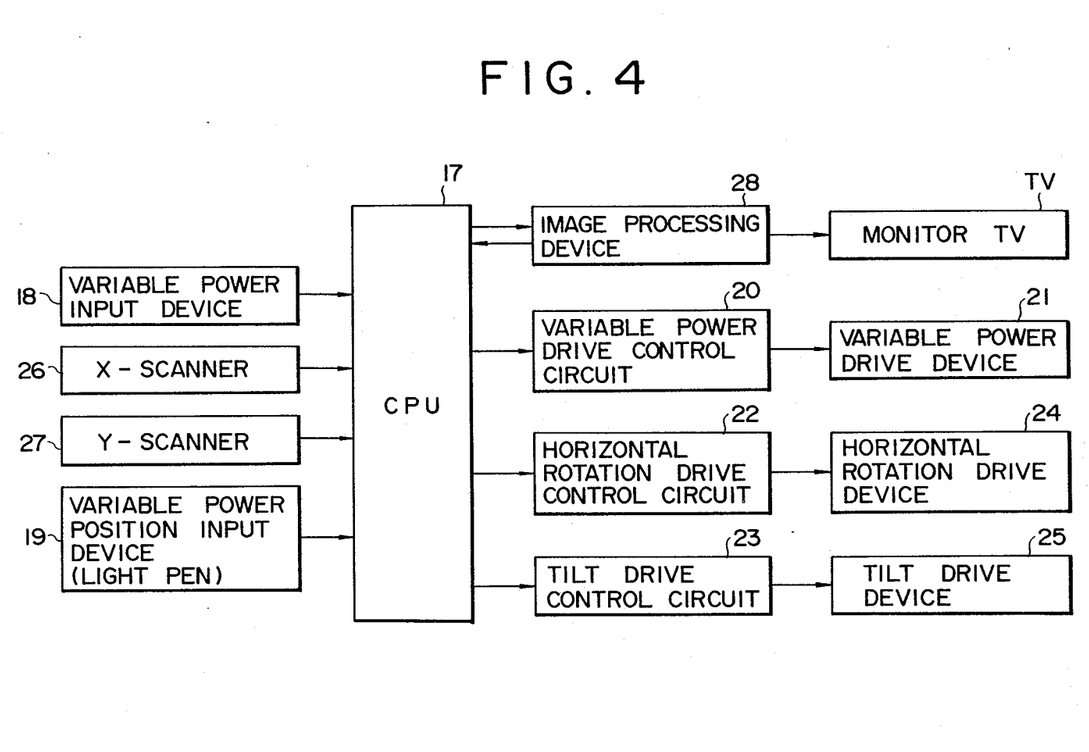
FIG. 4 is a schematic view for explaining a control circuit of the eye fundus camera of FIG. 1.
Figure 5:
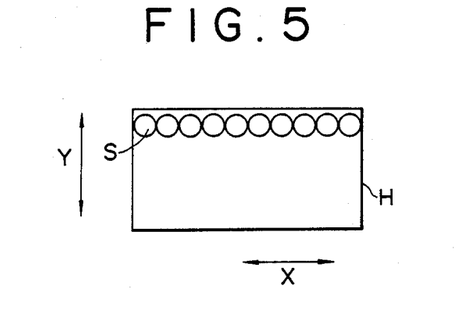
FIG. 5 and FIG. 6 are schematic views of the spot diameter of a scanning beam of light.
Figure 6:
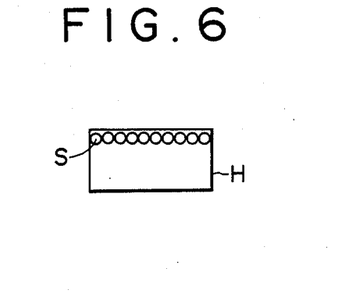

Also, the eye fundus camera includes such a control circuit as shown in FIG. 4. A CPU (central processing unit) 17 of this control circuit is input with a horizontal pivot angle signal from an X-scanner 26 and a pivot angle signal from a Y-scanner 27. The CPU 17 is further input with a variable power signal from a variable power input device 18 and with a variable power position from a variable power position input device 19 such as a light pen, etc.

Figure 8:
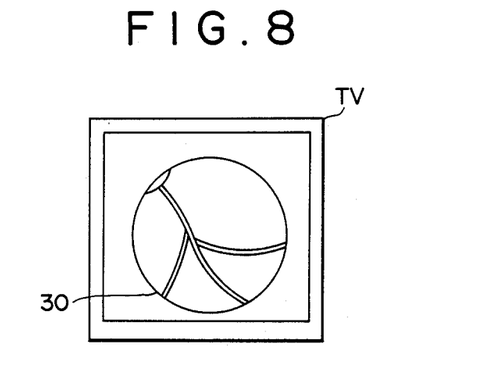

The X-scanner 26 includes the polygon mirror 7, a driver for the polygon mirror 7, pivot position (pivot angle) detecting means, etc., and the Y-scanner 27 includes the galvano mirror 10, a driver for the galvano mirror 10, pivot position detecting means, etc. And, according to the pivot position signal coming from the X-,Y-scanners 26,27, the CPU 117 controls and address circuit contained therein as such that the light quantity of reflected light of laser beam projected to the eye fundus and reflected from a spot S is sequentially stored in predetermined addresses of a memory of an image processing device 28 per predetermined distance (diameter of the spot S), and one frame portion information of the image of the eye fundus is stored in the memory. And, the image processing device 28 causes a television monitor TV to display an eye fundus image 29 according to the information stored in the memory as shown in FIG. 8. Since the constitution for such image processing is substantially the same to that of Japanese patent application No. Sho 62-130832 filed by the present applicant, detailed description thereof will be omitted.

Also, the CPU 17 inputs a control signal into a variable power drive control circuit 20 according to a variable power signal and causes the variable power drive control circuit 20 to control a variable power drive device 21. By this control, the variable power drive device 21 varies a combination of focal distances of the variable power lenses 8,9, thereby to vary a scanning angle of view H by laser beam and to vary the spot diameter S of laser beam from a state of FIG. 5 to a state of FIG. 6 or from the state of FIG. 6 to the state of FIG. 5. Since the procedure for varying the angle of view H is substantially the same to that of the above-mentioned Japanese patent application No. Sho 62-130832, detailed description thereof will be omitted.

Furthermore, the CPU 17 obtains a three-dimensional coordinate of the coordinate of the variable power position in accordance with the variable power position signal by regarding the coordinate of the original position as zero. And, the CPU 17 inputs a horizontal rotation control signal into a horizontal rotation control circuit 22 and a tilt signal into a tilt drive control circuit 23 in accordance with such obtained coordinate. This horizontal rotation drive control circuit 22 controls a horizontal rotation drive device 24 such as a pulse motor, etc. as such that the first optical part holding member 2 is rotated through a predetermined angle in the horizontal direction by the horizontal rotation driver. On the other hand, the tilt drive control circuit 23 controls a tilt drive device 25 as such that the second optical part holding member 3 is tilted through a predetermined angle in a vertical plane by the tilt drive device 25.

Figure 7:
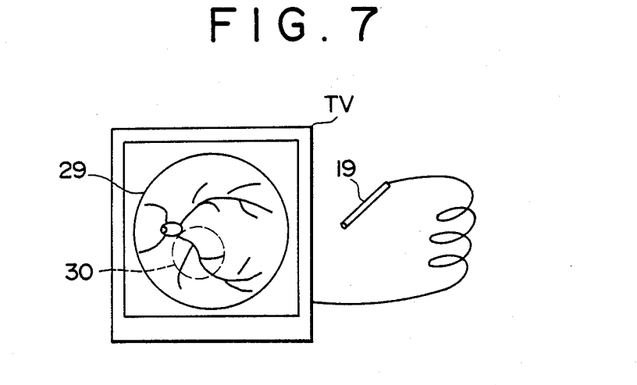
FIG. 7 and FIG. 8 are schematic views of an image of the eye fundus.

Therefore, in case the scope of the eye fundus image 29 shown by the broken line 30, for example, in FIG. 7 is enlarged, if the portion shown by this broken line 30 is input by the variable power position input device and if the variable power quantity is input by the variable power device, the angle of view H and the spot diameter S of the laser beam are varied, the first optical part holding member 2 is horizontally pivoted, the second optical part holding member 3 is tilted and only the part of the eye fundus image 29 shown by the broken line 30 in FIG. 8 is displayed in its enlarged scale as in FIG. 7.

Besides, the CPU 17 controls the reference scanning position $B_1$ of the galvano mirror 10 so as to be pivoted through $\frac{1}{2}$ of the tilt angle $\theta$ as shown by the broken line in the tilting direction of the tilt optical system according to the tilt angle $\theta$ (FIG. 9) of the tilt optical system in accordance with the tilting action of the second optical part holding member 3.

Figure 9:
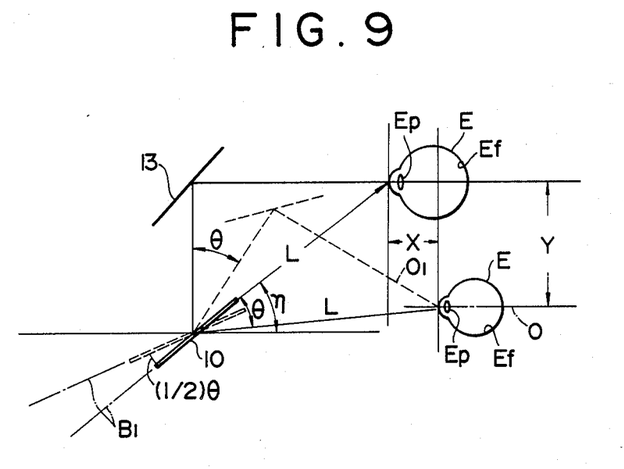
FIG. 9 is a schematic view of the tilt optical system of FIG. 1.

In case the tilt optical system is tilted through $\theta$ in this way, the objective lens 14 of the eye fundus camera and the correct position of the eye E are displaced in the direction approaching to and departing from the object lens 14 and in the vertical direction, respectively, as shown in FIG. 9. If the displacing quantity in the direction approaching to and departing from the objective lens 14 and in the vertical direction is represented by X, the displacing quantity of the eye E in the vertical direction by Y, the acute angle between an optical axis O of beam of light made incident to the galvano mirror 10 and the galvano mirror 10 by $\eta$, and the distance from the optical center (pivot center) 10a of the galvano mirror 10 to the anterior portion of the eye E by L, the displacing quantities X,Y when the tilt optical system is tilted through $\theta$ become as follows:

$$X = -L \cos \eta + L \cos(\eta - \theta)$$

$$Y = -L \sin \eta + L \sin(\eta - \theta)$$

Figure 3:
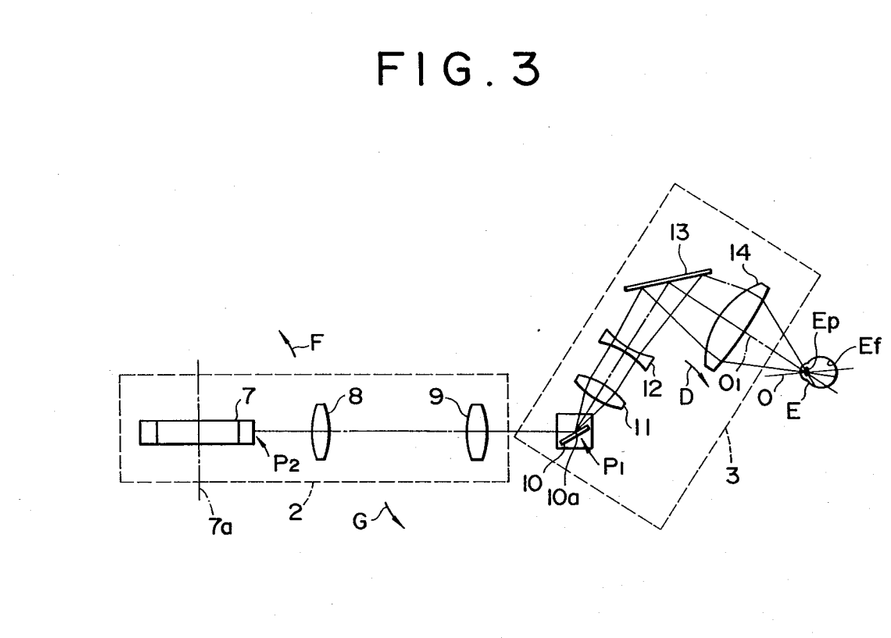
FIG. 3 is a schematic view showing the optical system, partly tilted, of FIG. 2.

Therefore, when the tilt optical system is going to be tilted, the body 1 of the eye fundus camera may be vertically and diagonally moved in parallel relation according to the displacing quantities X,Y as shown by the arrow in FIG. 3.

With the above-mentioned constitution, the laser beam scanning type eye fundus camera functions as follows.

Laser beam emitted by the laser light source 1 is made incident to the polygon mirror 7 through the lens 5 and the semitransparent mirror 6 and is then reflected toward the variable power lens 8 side. At this time, the reflecting beam is horizontally scanned by high speed rotation of the polygon mirror 7. The scanning beam, which has been horizontally scanned, is reflected by the galvano mirror 10 toward the relay lens 11 side through the variable power lenses 8,9 and is then projected to the eye fundus $E_f$ of the eye E and illuminate the same through the relay lens 11, the focus lens 12, the reflecting mirror 13 and the objective lens 14. At this time, the galvano mirror 10 is pivoted through a predetermined angle at a time per each horizontal scanning to cause the parallel scanning beam to be moved in the vertical direction to form a scanning plane of the laser beam on the eye fundus $E_f$. And, the laser beam projected to the eye fundus $E_f$ is reflected by the eye fundus $E_f$.

This reflected light is made incident to the objective lens 14, then guided in the direction opposite the progressing direction of the illuminating light along the common optical path with the illuminating optical system 2, i.e. the optical path starting from the objective lens 14 to the semitransparent mirror 6 and then guided to the light receiving element 15 through the semitransparent mirror 6 and the lens 16. And, the image processing device 28 displays the eye fundus image 29 on the monitor television TV according to the power output from the light receiving element 15.

In case the periphery of the eye fundus $E_f$, e.g., the lower portion of the eye fundus $E_f$ than the center thereof, is going to be observed and/or photographed, the second optical part holding member 3 as a lens barrel is pivoted (tilted) downward through $\theta$ about the optical center 10a of the galvano mirror 10 as shown by the arrow D in FIG. 3 in order to cause the optical axis $O_1$ of the objective lens 14 to be tilted downward with respect to the optical axis O of the eye E and to cause the body 1 to move, integrally and in parallel relation, through the displacing quantities X,Y leftward and upward at angles (the direction departing from the eye E) as shown by the arrow F in FIG. 3 to bring the optical axis $O_1$ into alignment with a lower portion of the eye fundus $E_f$.

Figure 2:
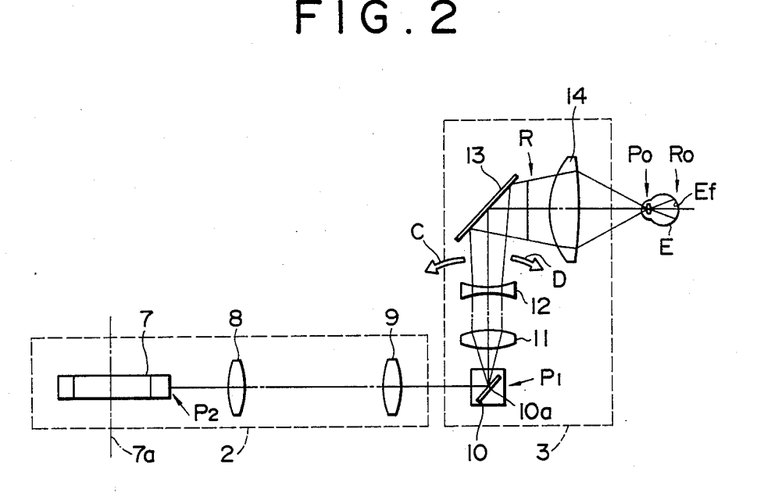
FIG. 2 is a side view of FIG. 1.

On the other hand, in case the periphery of the eye fundus $E_f$, e.g., the upper portion of the eye fundus $E_f$ than the center thereof, is going to be observed and/or photographed, the second optical part holding member 3 is pivoted (tilted) about the optical center 10a of the galvano mirror 10 in the direction as shown by the arrow C in FIG. 2 in order to cause the optical axis $O_1$ of the objective lens 14 to be tilted upward with respect to the optical axis O of the eye E and to cause the body 1 to move, in parallel relation, through the displacing quantities X,Y rightward and downward at angles (the direction approaching to the eye E) as shown by the arrow G in FIG. 3 to bring the optical axis $O_1$ into alignment with an upper portion of the eye fundus $E_f$.

In this way, if the second optical part holding member 2 is pivoted to cause the tilt optical system, which is held by the member 2, to be tilted and to cause the body 1 to be moved vertically and diagonally in association with the tilting operation of the tilt optical system, the optical axis $O_1$ can be brought into alignment with a predetermined position of the eye fundus $E_f$ with ease.

Also, there can be observed and/or photographed the right-hand and the left-hand peripheral portions of the eye fundus $E_f$ by making the first and the second optical part holding members 2,3 pivot horizontally about the center of rotation of the polygon mirror 7. Moreover, by performing this horizontally pivoting operation in accompany with the the afore-mentioned tilting operation, the diagonally upper and lower parts of the peripheral portion of the eye fundus $E_f$ can also be observed and/or photographed.

Figure 10:
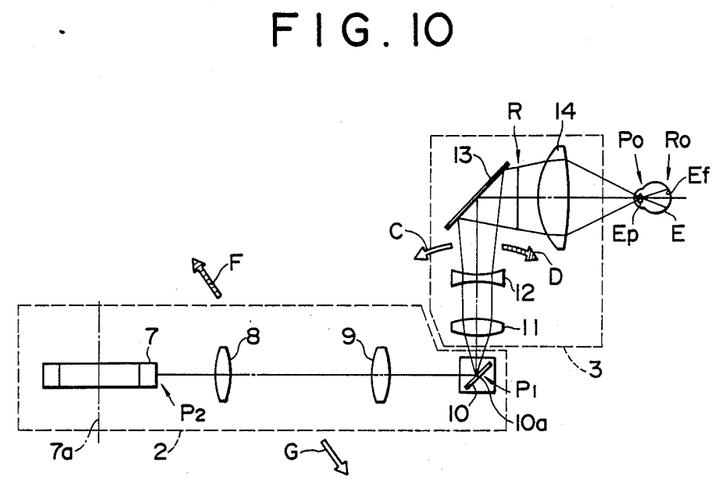
FIG. 10, FIG. 11 and FIG. 12 are schematic views showing other embodiments of the present invention.

FIG. 10 illustrates a second embodiment of the present invention. This embodiment shows an example, in which the optical parts from the polygon mirror 7 to the galvano mirror 10 are held by the first optical part holding member 2, the optical parts from the relay lens 11 to the objective lens 14 are held by the second optical part holding member 3 and a three-dimensional moving mechanism for moving the body 1 in the three-dimensional direction and tilt means of the tilt optical system are interlocked. In this case, the interlocking means, when the tilt optical system is tilted through angle $\theta$ by the tilt means, actuates the three-dimensional moving mechanism to cause the body 1 to move automatically, in parallel relation, by the displacing quantities X, Y diagonally upward and downward as shown by the arrows F, G. Such interlocking means may be mechanically constructed using a link mechanism or may be electrically constructed using the CPU 17 and the pulse motor.

And, in case the interlocking means is electrically constructed, it may be designed as such that the three-dimensional drive mechanism can be driven by the first pulse motor, and the second optical part holding member 3 can be pivoted (tilted) by the second pulse motor, the first and the second pulse motors being driven by the CPU 17. In this case, it may be designed as such that the tilt angle $\theta$ of the tilt optical system is detected by the CPU 17 with reference to the pivot control angle of the pulse motor and the pulse motor of the three-dimensional drive mechanism is driven by the CPU 17 in accordance with this tilt angle $\theta$, thereby to cause the body 1 to move automatically, in parallel relation, diagonally upward and downward through the displacing quantities X, Y as shown by the arrows F, G.

Figure 11:
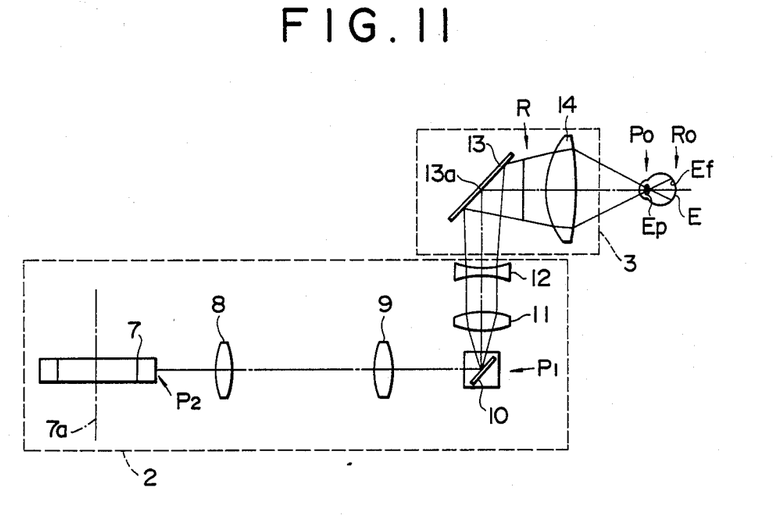

In the embodiments mentioned above, Although there have been described examples in which the optical members from the galvano mirror 10 to the objective lens 14 or the optical members from the relay lens 11 to the objective lens 14 can be pivoted (tilted) within a vertical plane about the optical center 10a of the galvano mirror 10 as a light reflector, the present invention is not necessarily limited to them. For example, as shown in FIG. 11, it may be designed as such that the optical parts from the polygon mirror 7 through the focus lens 12 are held by the first optical part holding member 2, and the reflecting mirror 13 and the objective lens 14 are held by the second optical part holding member 3, the tilt optical system comprising the reflecting mirror 13 and the objective lens 14 located immediately after the reflecting mirror 13 being tilted within a vertical plane about the optical center 13a of the reflecting mirror 13 as a light reflector.

Figure 12:
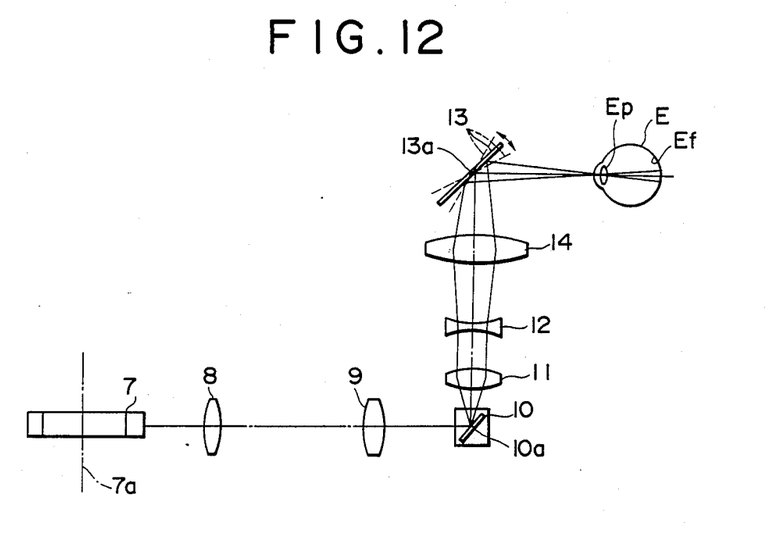

Also, as shown in FIG. 12, it may be designed as such that the objective lens 14 is located immediately before the reflecting mirror 13, i.e., between the reflecting mirror 13 and the focus lens 12 and only the reflecting mirror 13 is tilted as shown by the broken line, thereby to tilt the optical path from the reflecting mirror 13 to the eye E.

In the above embodiment, although the tilt optical path, i.e., only the tilt optical path is tilted, the present invention is not necessarily limited to this. For example, it may be designed as such that a light receiving optical system is provided in order to take out reflected light coming from the eye fundus from a midway of the tilt optical path, so that the reflecting beam of light is guided to the light receiving element through this light receiving optical system and this light receiving optical system is tilted together with the tilt optical system.

As described in the foregoing, an eye fundus camera according to one aspect of the present invention comprises a light source for illuminating an eye fundus to be tested, an illuminating optical system for projecting beam from the light source to the eye fundus, and a light receiving optical system for taking out the light reflected by the eye fundus through a common optical path with the illuminating optical system, the common optical path including a tilt optical path from a light reflector to the eye, the tilt optical system being tiltable about the optical center of the light reflector. Accordingly, the optical axis of the eye fundus camera can be tilted with respect to the optical axis of the subject's eye rapidly and easily. Moreover, this tilting prevents the tilting of the rotational axis of the polygon mirror, thus enabling to prevent an occurrence of inconveniences caused by the tilting of the rotational axis.

Also, an eye fundus camera according to another aspect of the invention comprises a polygon mirror being able to rotate at a high speed in order to scan beam coming from a light source in the horizontal direction, an illuminating optical system for projecting the scanned beam to an eye fundus to be tested, and a light receiving optical system for taking out the light reflected by the eye fundus through a common optical path with the illuminating optical system, a tilt optical path at least from a light reflector within the common optical path to the eye being tiltable about the optical center of the light reflector. Accordingly, the optical axis of the eye fundus camera can be tilted with respect to the optical axis of the eye rapidly and easily. Moreover, this tilting prevents the tilting of the rotational axis of the polygon mirror, thus enabling to prevent such inconveniences from occurring as wear of the bearing of the polygon mirror as in the prior art.

Furthermore, an eye fundus camera according to a further aspect of the present invention comprises an illuminating optical system for projecting illuminating beam from a light source to an eye fundus to be tested from a facing optical member opposite the eye, and a light receiving optical system including the facing optical member and adapted to take out light reflected by the eye fundus through a common optical path with the illuminating optical system, a tilt optical system at least from the facing optical member within the common optical path to a light reflector being tiltable about the optical center of the light reflector, the light reflector being connected to the tilt optical system as such that the light reflector is tilted in the tilting direction of the tilt optical system through ½ of a tilt angle of the tilt optical system about the optical center of the light reflector. Accordingly, the optical axis of the eye fundus camera can be tilted with respect to the optical axis of the eye easily with a simple structure, and the tilt optical system can be tilted to a predetermined position rapidly.

An eye fundus camera according to a still further aspect of the present invention comprises a polygon mirror being able to rotate at a high speed in order to scan illuminating beam from a light source in the horizontal direction, an illuminating optical system for projecting the scanned beam to an eye fundus to be tested from a facing optical member opposite the eye, and a light receiving optical system including the facing optical member and adapted to take reflected light from the eye fundus through a common optical path with the illuminating optical system, a tilt optical system from the facing optical member of the common optical path to a light reflector within the common optical path being tiltable about the optical center of the light reflector, the light reflector being connected to the tilt optical system as such that the light reflector being tilted in the tilting direction of the tilt optical system through ½ of a tilt angle of the tilt optical system about the optical center of the light reflector. Accordingly, the optical axis of the eye fundus camera can be tilted with respect to the optical axis of the eye rapidly and easily. Moreover, this tilting prevents the tilting of the rotational axis of the polygon mirror, thus enabling to prevent such inconvenience from occurring as wear of the bearing of the polygon mirror as in the prior art.

And, in case it is designed as such that the optical members from the polygon mirror to an optical member located immediately before the light reflector can be rotated about the center of rotation of the polygon mirror in the horizontal direction or in case it is designed as such that the optical members from the polygon mirror to the light reflector can be rotated about the center of rotation of the polygon mirror, the optical axis can be brought into alignment with the horizontal position of the eye fundus with ease.

Furthermore, in case the light reflector is a galvano mirror as a scanning member, the supporting point for the tilt optical system to be pivoted thereabout and the supporting point for the galvano mirror to be pivoted thereabout can be commonly used. As a result, since the supporting point for the tilt optical system becomes unecessary, a new part for the tilting is not required.

Furthermore, in case the light reflector is a reflecting mirror located immediately before the objective lens, or in case the light reflector is a reflecting mirror located immediately after the objective lense, the optical part used for tilting the tilt optical system can be limited to one in number. Therefore, the driving force required for the tilting can be reduced and thus the driving energy can be saved.

Moreover, in case it is designed as such that a body, which can be moved in the three dimensional direction by a three dimensional moving mechanism, is provided with the illuminating optical system and the light receiving optical system and also with interlocking means which, when the tilt optical systems is tilted through angle ζ and the position of the tilt optical system is displaced by X, Y in the vertical direction with respect to the eye, automatically causes the tilt body to be moved through displacing quantities X, Y in the vertical and diagnonal direction, the distance with respect to the optical axis of the tilt optical system and the eye due to tilting can be moved to the best position with respect to the eye.

Also, in case it is designed as such that the three dimensional drive mechanism can be driven by a first pulse motor, the tilt optical system can be tilted by a second pulse motor and both the pulse motors can be controlled by a CPU as interlocking means, the respective operating portions can be driven with a simple mechanism.

What is claimed is:

1. An eye fundus camera comprising:
   a light source for illuminating an eye fundus to be tested;
   an illuminating optical system for projecting a light beam from said light source to the eye fundus; and
   a light receiving optical system for taking out the light reflected by the eye fundus through a common optical path with said illuminating optical system, said common optical path including an objective lens;
said common optical path including a tilt optical path from a light reflector to the objective lens, said tilt optical system being tiltable about the optical center of said light reflector.

2. An eye fundus camera comprising:
a light source for illuminating an eye fundus to be tested;
a polygon mirror being able to rotate at a high speed in order to scan an illuminating beam from said light source in the horizontal direction;
an illuminating optical system for projecting the scanned illuminating beam to the eye fundus from a facing optical member opposite the eye; and
a light receiving optical system including the facing optical member and adapted to take out reflected light from the eye fundus through a common optical path with said illuminating optical system, said common optical path including an objective lens;
a tilt optical system from the facing optical member of the common optical path to a light reflector within the common optical path being tiltable about the optical center of the light reflector, the light reflector being connected to said tilt optical system such that the light reflector may be tilted in the tilting direction of said tilt optical system through ½ of a tilt angle of said tilt optical system about the optical center of the light reflector.

3. An eye fundus camera comprising;
a light source for illuminating an eye fundus to be tested;
an illuminating optical system for projecting illuminating beam from said light source to the eye fundus from a facing optical member opposite the eye; and
a light receiving optical system including the facing optical member and adapted to take out the light reflected by the eye fundus through a common optical path with said illuminating optical system;
a tilt optical system from the facing optical member of the common optical path to a light reflector within the common optical path being tiltable about the optical center of the light reflector, the light reflector being connected to the tilt optical system such that the light reflector is tilted in the tilting direction of said tilt optical system through ½ of a tilt angle of said tilt optical system about the optical center of the light reflector.

4. An eye fundus camera according to claim 3, wherein the light reflector is a galvano mirror as a scanning member.

5. An eye fundus camera comprising:
a light source for illuminating an eye fundus to be tested;
a polygon mirror being able to rotate at a high speed in order to scan a light beam coming from said light source in the horizontal direction and an illuminating optical system for projecting the scanned beam to the eye fundus; and
a light receiving optical system for taking out the light reflected by the eye fundus through a common optical path with the illuminating optical system, said common optical path including an objective lens;
a tilt optical path at least from a light reflector within the common optical path to the objective lens, said light reflector being tiltable about the optical center of said light reflector.

6. An eye fundus camera according to claim 5, wherein the optical members from the polygon mirror to the light reflector can be rotated about the center of rotation of the polygon mirror.

7. An eye fundus camera according to claim 5, wherein the light reflector is a reflecting mirror located immediately before the objective lens.

8. An eye fundus camera according to claim 5, wherein the light reflector is a reflecting mirror located immediately after the objective lens.

9. An eye fundus camera according to claim 5, further including a body movable in three dimensions by a three-dimensional moving mechanism, the body being provided with said illuminating optical system and said light receiving optical system and also with interlocking means which, when said tilt optical system is tilted through angle $\theta$ and the position of said tilt optical system is displaced by X, Y in the vertical direction with respect to the eye, automatically causes the body to be moved through displacing quantities X, Y in the vertical and diagonal directions.

10. An eye fundus camera according to claim 9, wherein the three-dimensional drive mechanism can be driven by a first pulse motor and the tilt optical system can be tilted by a second pulse motor, both the pulse motors being driven by a CPU as interlocking means.

11. An eye fundus camera according to claim 5 or claim 2, wherein the optical members from the polygon mirror to an optical member located immediately before the light reflector can be rotated about the center of rotation of the polygon mirror in the horizontal direction.

12. An eye fundus camera according to claim 11, wherein the optical members from the polygon mirror to the light reflector are rotatable about the center of rotation of the polygon mirror.

13. An eye fundus camera according to claim 11, wherein the light reflector is a reflecting mirror located immediately before the objective lens.

14. An eye fundus camera according to claim 11, wherein the light reflector is a reflecting mirror located immediately after the objective lens.

15. An eye fundus camera according to claim 11, further including a body movable in three dimensions by a three-dimensional moving mechanism, the body being provided with said illuminating optical system and said light receiving optical system and also with interlocking means which, when said tilt optical system is tilted through angle $\theta$ and the position of said tilt optical system is displaced by X, Y in the vertical direction with respect to the eye, automatically causes the body to be moved through displacing quantities X, Y in the vertical and diagonal directions.

16. An eye fundus camera according to claim 15, wherein the three-dimensional drive mechanism can be driven by a first pulse motor and the tilt optical system can be tilted by a second pulse motor, both the pulse motors being driven by a CPU as interlocking means.

* * * * *